(12) United States Patent
Sugioka

(10) Patent No.: US 8,900,173 B2
(45) Date of Patent: Dec. 2, 2014

(54) BLOOD PURIFICATION APPARATUS

(75) Inventor: Akira Sugioka, Makinohara (JP)

(73) Assignee: Nikkiso Company Limited, Tokyo (JP)

( * ) Notice: Subject to any disclaimer, the term of this patent is extended or adjusted under 35 U.S.C. 154(b) by 0 days.

(21) Appl. No.: 13/569,565

(22) Filed: Aug. 8, 2012

(65) Prior Publication Data

US 2013/0030347 A1 Jan. 31, 2013

Related U.S. Application Data

(63) Continuation of application No. PCT/JP2011/052753, filed on Feb. 9, 2011.

(30) Foreign Application Priority Data

Feb. 10, 2010 (JP) ................................. 2010-028183

(51) Int. Cl.
| | |
|---|---|
| *B01D 36/00* | (2006.01) |
| *B01D 61/00* | (2006.01) |
| *B01D 61/24* | (2006.01) |
| *A61M 1/14* | (2006.01) |
| *A61M 1/34* | (2006.01) |

(52) U.S. Cl.
CPC ............. *A61M 1/342* (2013.01); *A61M 1/3465* (2014.02); *A61M 2205/14* (2013.01)
USPC ........ 604/6.09; 604/4.01; 604/5.01; 210/646; 210/767

(58) Field of Classification Search
CPC ...... B01D 36/00; B01D 36/003; B01D 61/00; B01D 61/24; B01D 61/243; A61M 1/14

USPC ................ 604/6.09, 4.01, 5.01; 210/646, 767
See application file for complete search history.

(56) References Cited

U.S. PATENT DOCUMENTS

| | | | | |
|---|---|---|---|---|
| 4,493,693 A | * | 1/1985 | Bilstad et al. ................. | 604/6.09 |
| 4,828,543 A | * | 5/1989 | Weiss et al. ................... | 604/6.09 |
| 4,846,787 A | * | 7/1989 | Aall-Flood et al. .......... | 604/6.09 |

(Continued)

FOREIGN PATENT DOCUMENTS

| | | |
|---|---|---|
| JP | 02-289259 | 11/1990 |
| JP | 2004-313522 | 11/2004 |

(Continued)

OTHER PUBLICATIONS

Machine translation of JP 2004-313522 A, retrieved form JPO on Jan. 22, 2013.*

*Primary Examiner* — Tatyana Zalukaeva
*Assistant Examiner* — Sara Sass
(74) *Attorney, Agent, or Firm* — Harness, Dickey & Pierce, P.L.C.

(57) ABSTRACT

A blood purification apparatus has a dialyzer (1), an arterial blood circuit (2) with a blood pump (4), a venous blood circuit (3), a dialysis fluid introduction line (L1), a dialysis fluid discharge line (L2), a dialysate infusing line (L8), and a dialysate infusing pump (13). A closed circuit is formed in the flow route of the dialysis fluid on the dialysis fluid introduction line (L1) side including a predetermined part where a collection port (11) is formed. A testing process is performed to confirm the connection of the dialysate infusing line (L8) to the collection port (11) by measuring fluid pressure within the closed circuit while driving the dialysate infusing pump (13).

5 Claims, 4 Drawing Sheets

(56) References Cited

U.S. PATENT DOCUMENTS

| | | | | |
|---|---|---|---|---|
| 4,923,598 | A | * | 5/1990 | Schal .............................. 210/87 |
| 6,916,424 | B2 | | 7/2005 | Collins et al. |
| 2009/0095679 | A1 | * | 4/2009 | Demers et al. ................ 210/646 |

FOREIGN PATENT DOCUMENTS

| | | | |
|---|---|---|---|
| JP | 2004313522 A | * | 11/2004 |
| JP | 2005-218709 | | 8/2005 |
| WO | WO2009/060741 | | 5/2009 |

* cited by examiner

BLOOD PURIFICATION APPARATUS

CROSS-REFERENCE TO RELATED APPLICATIONS

This application is a continuation of International Application No. PCT/JP2011/052753, filed Feb. 9, 2011, which claims priority to Japanese Application No. 2010-028183, filed Feb. 10, 2010. The disclosures of the above applications are incorporated herein by reference.

FIELD

The present disclosure relates to a blood purification apparatus that performs a blood purification treatment using a blood purifier connected to a blood circuit.

BACKGROUND

Recently, in dialysis apparatus, such as a blood purification apparatus, a technique has been suggested that performs priming, reinfusion, and dialysate infusion (emergency dialysate infusion) using a dialysate supplied to a dialyzer during dialysis treatment (particularly, an on-line HDF or an on-line HF). Japanese Laid-open Patent Publication No. 2004-313522 discloses a dialysis apparatus that includes a dialysate infusing line. One end is connected to a collection port formed in a predetermined part of a dialysate introduction line. The other end is connected to a blood circuit (arterial blood circuit or venous blood circuit), with a dialysate infusing pump disposed in the dialysate infusing line. In order to perform priming, the reinfusion or the dialysate infusion, the emergency dialysate infusion, using the dialysis apparatus, the dialysate in a dialysate introduction line is supplied to the blood circuit, arterial blood circuit or venous blood circuit, by driving the dialysate infusing pump.

SUMMARY

However, in the blood purification apparatus of the related art, in order to perform priming, the reinfusion or the dialysate infusion (the emergency dialysate infusion), there is a need to connect one end of the dialysate infusing line to the collection port formed in a predetermined part of the dialysate introduction line. Thus, a worker needs to visually confirm whether or not the connection is normally performed. For this reason, there is a concern of human error, such as forgetting to confirm the connection confirmation.

The present disclosure has taken into account these circumstances, and provides a blood purification apparatus capable of preventing forgetting of the dialysate infusing line connection by automatically performing the connection confirmation of the dialysate infusing line to the collection port, formed in a predetermined part of the dialysate introduction line.

According to the disclosure, a blood purification apparatus is provided that includes a blood purifier with a blood purification membrane that performs blood purification. An arterial blood circuit has a proximal end that is connected to the blood purifier. A blood pump is disposed in the middle of the arterial blood circuit. A venous blood circuit has a proximal end that is connected to the blood purifier. A dialysate introduction line introduces a dialysate into the blood purifier. A dialysate discharge line discharges the dialysate from the blood purifier. A dialysate infusing line has one end that is connected to a collection port formed in a predetermined part of the dialysate introduction line. The other end is connected to the arterial blood circuit or the venous blood circuit. A dialysate infusing pump is disposed in the dialysate infusing line and is able to supply the dialysate of the dialysate introduction line to the arterial blood circuit or the venous blood circuit. A closed circuit is formed in a flow route of the dialysate of the dialysate introduction line side including the predetermined part formed with the collection port. A test process is performed to confirm the connection of the dialysate infusing line to the collection port by measuring a fluid pressure in the closed circuit while driving the dialysate infusing pump.

The blood purification apparatus includes a clamp device, capable of opening and closing the flow route, disposed in the dialysate infusing line. The connection confirmation of the dialysate infusing line and the opening and closing confirmation of the clamp device can be performed in the test process.

The blood purification apparatus includes a positive pressure applied to the closed circuit by driving the dialysate infusing pump in reverse rotation direction in the test process.

The blood purification apparatus includes a measurement device capable of measuring the fluid pressure in the closed circuit state when the dialysate infusing pump is driven in the test process. A determination device determines whether or not the dialysate infusing line is connected normally to the collection port based on the measured value of the measurement device.

The closed circuit is formed in a flow route of the dialysate of the dialysate introduction line side that includes the predetermined part formed with the collection port. A test process is performed to confirm the connection of the dialysate infusing line to the collection port, by measuring the fluid pressure in the closed circuit while driving the dialysate infusing pump. Thus, it is possible to prevent the forgetting of the dialysate infusing line connection by automatically performing the connection confirmation of the dialysate infusing line to the collection port.

The clamp device, capable of opening and closing the flow route, is disposed in the dialysate infusing line. The connection confirmation of the dialysate infusing line and the opening and closing confirmation of the clamp device can be performed in the test process. Thus, it is possible to prevent the forgetting of the clamp device opening operation in addition to the prevention of the forgetting of the dialysate infusing line connection. Further, it is possible to more reliably perform circulation of the dialysate in the dialysate infusing line.

A positive pressure is applied to the closed circuit by driving the dialysate infusing pump in a reverse rotation direction in the test process. Thus, when performing the connection confirmation of the dialysate infusing line to the collection port, it is possible to more reliably confirm a case where the connection is not normal.

The apparatus includes a measurement device and a determination device. The measurement device is capable of measuring the fluid pressure in the closed circuit state where the dialysate infusing pump is driven in the test process. The determination device determines whether or not the dialysate infusing line is connected normally to the collection port based on the measured value of the measurement device. Thus, it is possible to more accurately and automatically perform the connection confirmation of the dialysate infusing line to the collection port.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Hereinafter, an embodiment of the present disclosure will be specifically described with reference to the drawings.

Figure 1:
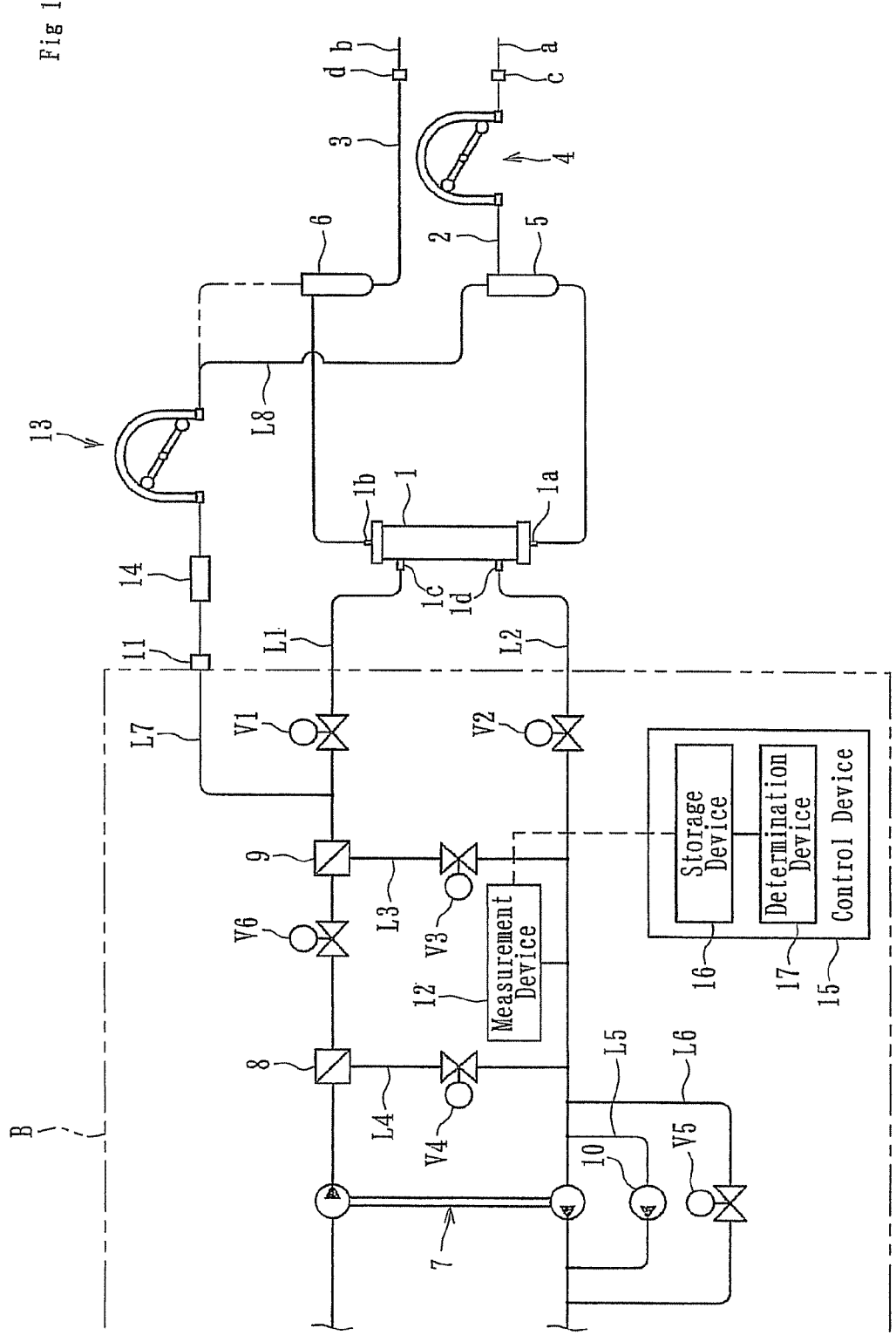
FIG. 1 is a schematic diagram of a dialysis apparatus according to an embodiment of the present disclosure.

A blood purification apparatus according to the present embodiment is applied to a blood dialysis apparatus. As shown in FIG. 1, the blood purification apparatus mainly includes a blood circuit and a dialysis apparatus main body B. The blood circuit includes an arterial blood circuit 2 and a venous blood circuit 3 connected to a dialyzer 1, as a blood purifier. The dialysis apparatus main body B has a dialysate introduction line L1, a dialysate discharge line L2, a dialysate infusing line L8, a measurement device 12, a dialysate infusing pump 13, and a control device 15.

The dialyzer 1 includes a blood purification membrane (not shown). The membrane is a hollow fiber type blood dialysis filtration membrane. The membrane includes a flat membrane type, blood dialysis membrane and a blood filtration membrane. The dialyzer 1 is formed with a blood introduction port 1a to introduce the blood. A blood delivery port 1b delivers the introduced blood. A dialysate introduction port 1c introduces the dialysate. A dialysate discharge port id discharges the introduced dialysate. The dialyzer 1 purifies the blood by bringing the dialysate into contact with the blood introduced from the blood introduction portion 1a via a hollow fiber.

The arterial blood circuit 2 includes a flexible tube. One end of the tube is connected to the blood introduction port 1a of the dialyzer 1 to guide the blood collected from a patient's blood vessel into the hollow fiber of the dialyzer 1. The other end of the arterial blood circuit 2 has a connector (c) capable of attaching an arterial puncture needle (a). An arterial air trap chamber 5 is connected in the middle. A blood pump 4 is also disposed onto the tube. Furthermore, the blood pump 4 is a peristaltic type pump. The pump has a configuration that squeeze the flexible tube when rotated forward to cause the blood to flow from the arterial puncture needle (a) in the direction of the blood introduction port 1a of the dialyzer 1.

The venous blood circuit 3 includes a flexible tube as in the arterial blood circuit 2. One end of the tube is connected to the blood delivery port 1b of the dialyzer 1 to introduce the blood passing through the hollow fiber. The other end of the venous blood circuit 3 has a connector (d) capable of attaching a venous puncture needle (b). A venous air trap chamber 6 is connected in the middle of the venous blood circuit. The patient's blood is collected by the arterial puncture needle and reaches the dialyzer 1 via the arterial blood circuit 2. After the blood purification is performed, the blood flows though the venous blood circuit 3, and returns back to the body of the patient via the venous puncture needle b. Thus, the extracorporeal circulation is performed.

The dialysate introduction line L1 and the dialysate discharge line L2 are connected to the dialysate introduction port 1c and the dialysate discharge port 1d of the dialyzer 1, respectively. The dialysate introduced to the dialyzer 1, via the dialysate introduction line L1, can be discharged from the dialysate discharge line L2 through the outside of the hollow fiber. An electromagnetic valve V1 and an electromagnetic valve V2 are connected to the middle of the dialysate introduction line L1 and the dialysate discharge line L2, respectively.

A duplex pump 7 supplies the dialyzer 1 with the dialysate, prepared to a predetermined concentration, and discharges the dialysate from the dialyzer 1. The duplex pump 7 is connected to the dialysate introduction line L1 and the dialysate discharge line L2. Filtration filters 8 and 9, as well as the electromagnetic valve V1, are connected between the duplex pump 7 in the dialysate introduction line L1. The filtration filters 8 and 9 filter and purifies the dialysate flowing through the dialysate introduction line L1. Bypass lines L3 and L4, formed with the filtration filters 8 and 9, guide the dialysate so as to bypass the dialysate discharge line L2. Electromagnetic valves V3 and V4 are connected to the bypass lines L3 and L4, respectively. Furthermore, an electromagnetic valve V6 is connected between the filtration filter 8 and the filtration filter 9 in the dialysate introduction line L1.

Measurement device 12, capable of measuring the fluid pressure of the dialysate, is connected in the dialysate discharge line L2, between the connection section of the bypass line L3 and the connection section of the bypass line L4. The dialysate discharge line L2 is formed with bypass lines L5 and L6 that bypass the duplex pump 7. An ultrafiltration pump 10, to remove the water content from the patient's blood flowing in the dialyzer 1, is disposed in the bypass line L5. The electromagnetic valve V5, capable of opening or closing the flow route, is disposed in the bypass line L6. A closed circuit mentioned below can be formed by arbitrarily and selectively opening and closing the electromagnetic valves V1 to V6.

One end of the dialysate infusing line L8 is connected to a collection port 11 formed in a predetermined part, a tip of a branch line L7 branched from the dialysate introduction line L1 in the present embodiment, of the dialysate introduction line L1. The other end is constituted by a flow route connected to the arterial air trap chamber 5 of the arterial blood circuit 2 or the venous air trap chamber 6 of the venous blood circuit 3 as shown by a two-dot chain line in FIG. 2.

The dialysate infusing line L8 included clamp device 14 that is capable of opening and closing the flow route. After the dialysate infusing line L8 is connected to the collection port 11, by a worker, the clamp device 14 is in a closed state until the dialysate is caused to circulate, and the flow route is closed. Moreover, if necessary during priming, reinfusion, dialysate infusion or the like, the clamp device 14 is moved into an open state by a worker. Thus, the dialysate introduction line L1 communicates with the blood circuit (the arterial blood circuit 2 or the venous blood circuit 3).

Figure 3:
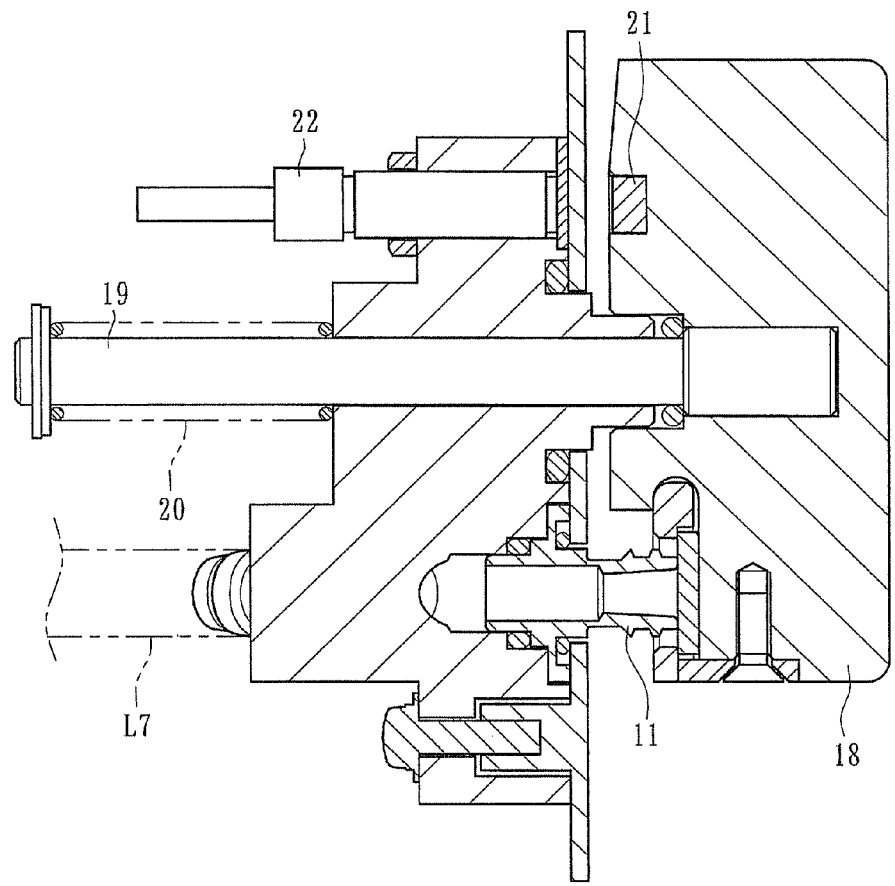
FIG. 3 is a cross-sectional schematic diagram of a collection port in the dialysis apparatus.

The collection port 11 is formed by a port formed in the dialysis apparatus main body B. The collection port 11 can be opened and closed by a lid member 18 that can be rotated around a shaft 19, as shown in FIG. 3. Specifically, the lid member 18 can be rotated between a closed position that covers the collection port 11 and an open position that causes the collection port 11 to face outside. When in the closed position, it closes an opening end of the collection port 11 by the biasing force of a spring 20.

Figure 4:
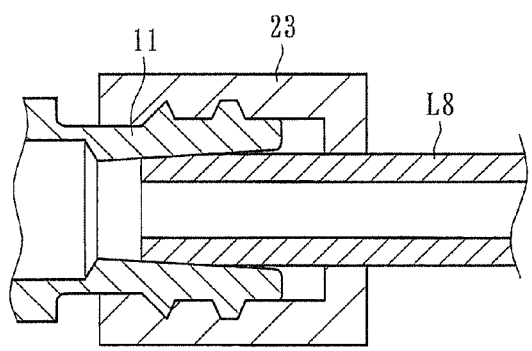
FIG. 4 is a cross-sectional schematic diagram of a state where a dialysate infusing line is connected to the collection port.

The lid member 18 can be shifted from the closed position to the open position by moving the lid member 18, held in the closed position, to the right direction of the drawings against biasing force of the spring 20 and rotating the lid member 18 around the shaft 19. In that state, as shown in FIG. 4, one end of the dialysate infusing line L8 is connected to the collection port 11. As shown in FIG. 4, the one end of the dialysate infusing line L8 is formed with a connector member 23. Thus, it is possible to firmly connect the collection port 11 and the one end of the dialysate infusing line L8 by screwing a female screw section formed in the connector member 23 with a male screw section formed in the collection port 11 in a state of fitting the one end into the collection port 11.

A magnet 21 is formed in a predetermined part of the lid member 18. The magnet 21 is capable of generating a magnetic force. A lead switch 22 is disposed in the main body B. The lead switch 22 is capable of detecting a magnetic force in a position opposing the magnet 21. The lead switch 22 generates an electrical on-off signal when the lid member 18 is in the closed position. As a result, it is possible to detect whether the lid member 18 is in the closed position or the opened position, based on the on signal or the off signal of the lead switch 22.

The dialysate infusing pump 13 is disposed in the dialysate infusing line L8. The pump 13 is able to supply the dialysate of the dialysate introduction line L1 to the blood circuit, the arterial blood circuit 2 or the venous blood circuit 3. Like the blood pump 4, the dialysate infusing pump 13 is a peristaltic type pump. It is configured to squeeze the tube constituting the dialysate infusing line L8 when it is rotated forward to allow the dialysate to flow. Additionally, the dialysate infusing pump 13 is able to be rotated forward and reverse.

The control device 15 is formed from, for example, a microcomputer or the like that can control the opening and closing of the various electromagnetic valves V1 to V6 disposed in the dialysis apparatus and control an actuator of the blood pump 4, the dialysate infusing pump 9 or the like. Particularly, in the present embodiment, the control device 15 is formed with a storage device 16, a determination device 17 or the like and performs the test process for the connection confirmation of the dialysate infusing line L8 to the collection port 11 and the opening and closing confirmation of the clamp device. The test process is a process for performing the connection confirmation of the dialysate infusing L8 to the collection port 11 and the opening and closing confirmation of the clamp device 14. The process measures the fluid pressure in the closed circuit by the measurement device 12 while driving the dialysate infusing pump 13. The dialysate infusing pump 13 is in a state where, in the flow route, that is a branch line L7, the dialysate introduction line L1 and the dialysate discharge line L2 or the flow route of the dialysate in the dialysis apparatus main body B branched from the lines, of the dialysate of the dialysate introduction line L1 including a predetermined part formed with the collection port 11 is formed with the closed circuit.

The closed circuit in the test process is formed by the electromagnetic valves V1, V2, V4, V5 and V6 in the closed state and the electromagnetic valve V3 in the opened state. Thus, it is possible to measure the fluid pressure, the fluid pressure of the dialysate, in the closed circuit by the measurement device 12. Furthermore, the closed circuit may be configured to include the part formed with the measurement device 12. For example, it may be formed by the electromagnetic valves V1, V2 and V5 in the closed state and the electromagnetic valves V3, V4 and V6 in the opened state.

The measurement device 12, according to the present embodiment, is able to measure the fluid pressure in the closed circuit state while driving the dialysate infusing pump 13 in the test process. The measurement device 12 is electrically connected to the storage device 16 of the control device 15. The storage device 16 is able to store a measured value, e.g., the fluid pressure measured by the measurement device 12 during the test process. The storage device is connected to the determination device 17. The determination device 17, based on the measured value of the measurement device 12 stored in the storage device 16, determines whether or not the dialysate infusing line L8 is connected normally to the collection port 11 or the clamp device 14 is in the opened state.

That is, in a case where the dialysate infusing line L8 is not connected normally to the collection port 11, when driving (the normal rotation driving or the reverse rotation driving) the dialysate infusing pump 13 in the test process, giving the positive pressure or the negative pressure to the closed circuit enables stopping of the dialysate infusing pump 13. The fluid pressure measured by the measurement device 12 is reduced over time. If the determination device 17 determines a decrease in fluid reduction, it is possible to determine that the connection to the collection port 11 is not normal. Furthermore, in a case where the clamp device 14 is not in the opened state, similarly, a case where the dialysate infusing line L8 is not completely connected to the collection port 11 and the collection port 11 is in the opened state, even when driving (forward rotation driving or reverse rotation driving) the dialysate infusing pump 13 in the test process, the positive pressure or the negative pressure cannot be applied to the closed circuit. The measure value is different from an initial value. Thus, when the determination device 17 determines that state, it is possible to determine that the clamp device 14 is not in the opened state.

In the present embodiment, the positive pressure is applied to the closed circuit by driving the dialysate infusing pump 13 in the reverse rotation direction in the test process. As a result, when driving the dialysate infusing pump 13 in the reverse rotation direction to apply a positive pressure, for example, in a case where the fitting of one end of the dialysate infusing line L8 to the collection port 11 is defective, or in a case where a screw fitting using the connector member 23 is defective, the one end of the dialysate infusing line L8 is separated from the collection port 11 by the applied positive pressure. Thus, the pressure measured by the measurement device 12 is reduced. Accordingly, the connection defect can be more accurately detected.

Figure 5:
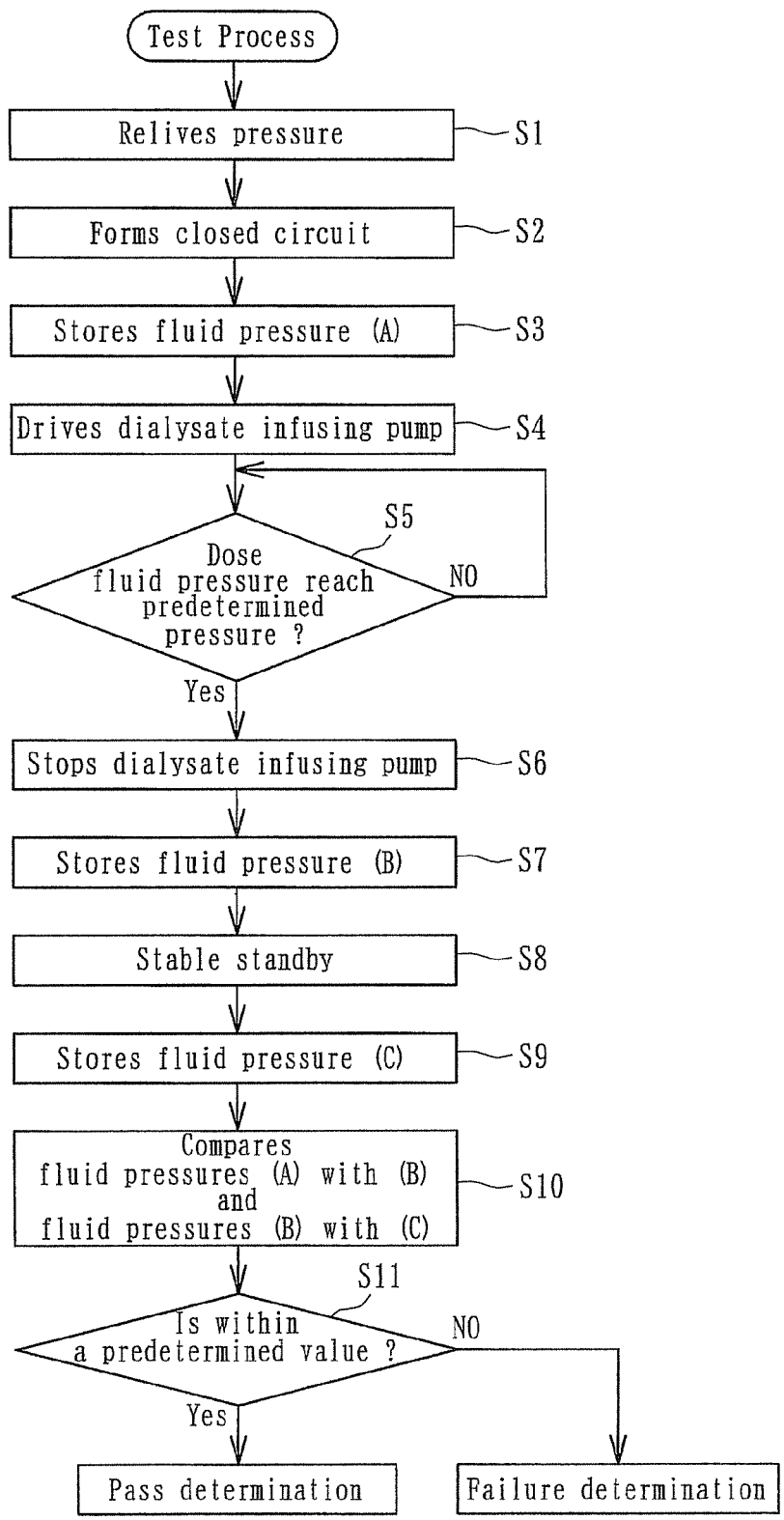
FIG. 5 is a flowchart that shows a control content of the test process in the dialysis apparatus.

Hereinafter, the control contents of the control device 15 in the test process will be described based on a flowchart of FIG. 5.

Figure 2:
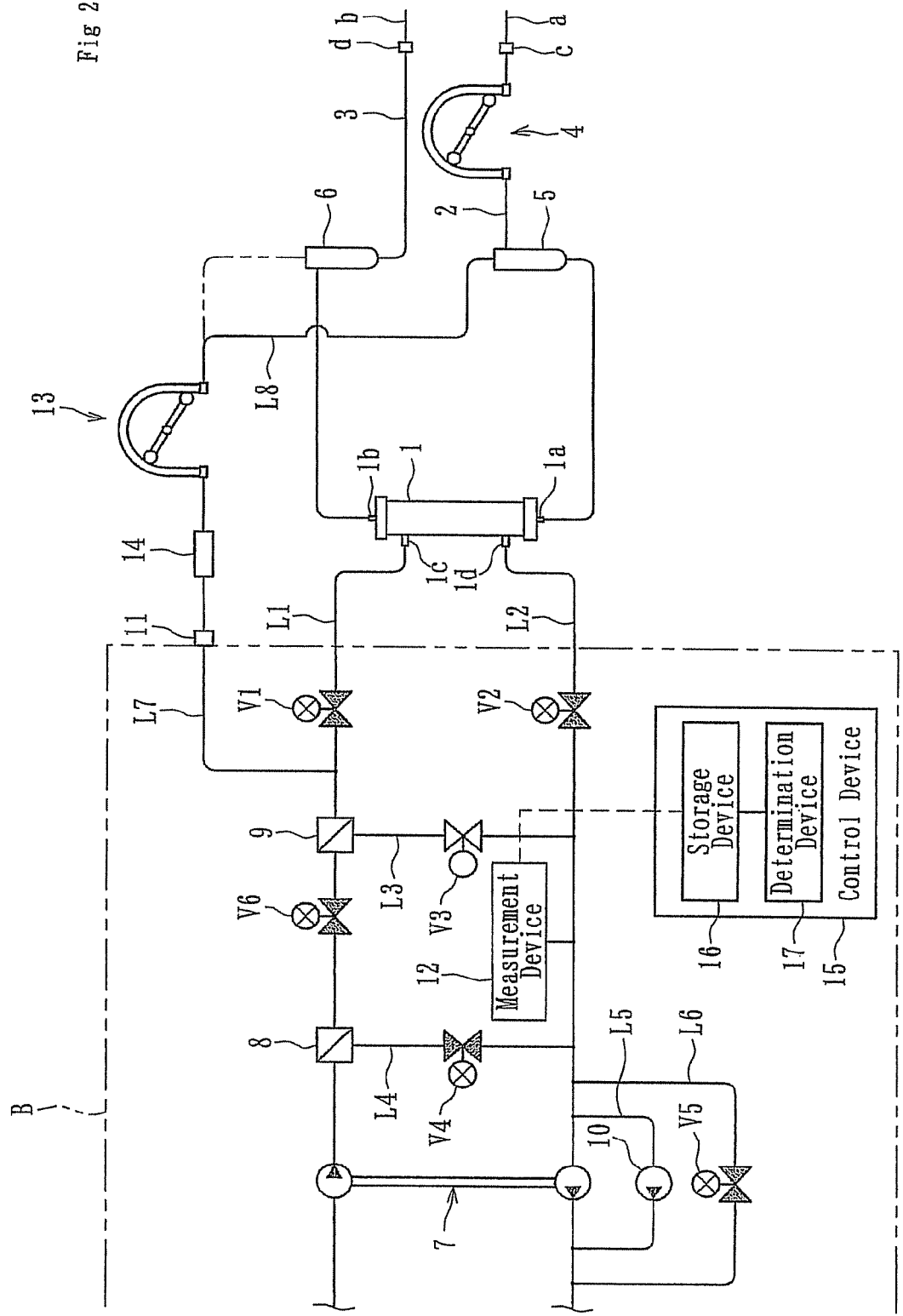
FIG. 2 is a schematic diagram that shows a state when a test process is performed in the dialysis apparatus.

First, the pressure is relieved by the electromagnetic valves V3, V4 and V5 in the opened state (S1). After that, as shown in FIG. 2, a mechanism for forming a closed circuit includes the electromagnetic valves V1, V2, V4, V5 and V6 in the closed state and the electromagnetic valve V3 in the opened state. Thus, the closed circuit is formed (S2). A fluid pressure (A) is measured by the measurement device 12 in the state and is stored in the storage device 16 (S3). The dialysate infusing pump 13 is driven, in the reverse rotation driving direction, in the present embodiment (S4). A determination is made as to whether the fluid pressure measured by the measurement device 12 reaches a predetermined pressure (S5). In the present embodiment, whether or not the fluid pressure reaches a predetermined fluid pressure is determined in S5. Whether or not a predetermined time elapses or the dialysate infusing pump 13 is rotated by a predetermined amount may be determined. The determinations may be combined and performed.

When it is determined that the fluid pressure measured by the measurement device 12 in S5 reaches a predetermined fluid pressure, the process proceeds to S6. The dialysate infusing pump 13 is stopped (S6). In that state, the measured value, the fluid pressure, of the measurement device 12 is stored in the storage device 16 and is set to the fluid pressure (B) (S7). The stable standby is performed for a predetermined time, for example, about 4 seconds (S8). If the standby time in S8 is set to be longer, the accuracy can be enhanced. The measured value, the fluid pressure, of the measurement device 12 is stored in the storage device 16 and is set to the fluid pressure (C) (S9).

After that, the determination device 17 compares the fluid pressure (A) stored in the storage device 16 to the fluid pressure (B). The fluid pressure (B) is compared to the fluid pressure (C) (S10). A determination is made as to whether or not the pressurization is performed normally based on the comparison of the fluid pressure (A) and the fluid pressure (B). It is determined whether or not leakage exists based on the comparison of the fluid pressure (B) and the fluid pressure (C) (S11). Furthermore, if it is determined that the pressurization is performed normally and there is no leakage, the result is determined as a pass. It is recognized that the connection of the dialysate infusing line L8 to the collection line 11 is normal. Meanwhile, if it is determined that the pressurization is not normally performed or there is a leakage, the result is determined as a failure. It is recognized that the connection of the dialysate infusing line L8 to the collection line 11 is not normal.

According to the configuration mentioned above, the closed circuit is formed in the flow route of the dialysate of the dialysate introduction line L1 side including a predetermined part formed with the collection port 11. The test process for the connection confirmation of the dialysate infusing line L8 to the collection port 11 is performed by measuring the fluid pressure in the closed circuit while driving the dialysate infusing pump 13. Thus, the connection confirmation of the dialysate infusing line L8 to the collection port 11 is automatically performed. Thus, it is possible to prevent the forgetting of the dialysate infusing line L8 connection.

The dialysate infusing line L8 includes the clamp device 14 capable of opening and closing the flow route. The connection confirmation of the dialysate infusing line L8 and the opening and closing confirmation of the clamp device 14 can be performed in the test process. Thus, it is possible to prevent the forgetting of the clamp device 14 opening operation in addition to the prevention of the forgetting of the dialysate infusing line L8 connection. Accordingly, it is possible to more reliably perform the circulation of the dialysate in the dialysate infusing line L8.

A positive pressure is applied to the closed circuit by driving the dialysate infusing pump 13 in the reverse rotation direction in the test process when performing the connection confirmation of the dialysate infusing line L8 to the collection port 11. Thus, it is possible to more accurately perform the confirmation of a case where the connection is not normal. The apparatus includes the measurement device 12 that is capable of measuring the fluid pressure in the closed circuit state while driving the dialysate infusing pump 13 in the test process. The determination device 17 determines whether or not the dialysate infusing line L8 is connected normally to the collection port 11 based on the measured value of the measurement device 12. Thus, it is possible to more accurately and automatically perform the connection confirmation of the dialysate infusing line L8 to the collection port 11.

Although the present disclosure has been described as above, the present disclosure is not limited thereto, but, for example, a negative pressure may be applied to the closed circuit by driving the dialysate infusing pump 13 in the forward rotation direction in the test process. The measurement device 12, for measuring the fluid pressure, may be disposed in the closed circuit formed in the test process, and, for example, may be connected to the branch line L7 and the dialysate introduction line L1. In the present embodiment, although the other end of the dialysate infusing line L8 is connected to the arterial air trap chamber 5 of the arterial blood circuit 2 or the venous air trap chamber 6 of the venous blood circuit 3, the other end of the dialysate infusing line L8 may be connected to other parts of the arterial blood circuit 2 or the venous blood circuit 3.

If a blood purification apparatus is configured so that a closed circuit is formed in the flow route of the dialysate of the dialysate introduction line side including a predetermined part formed with a collection port, the test process for the connection confirmation of the dialysate infusing line to the collection port can be performed by measuring the fluid pressure in the closed circuit while driving the dialysate infusing pump. The apparatus can also be applied to blood purification apparatus with other added functions or the like.

The present disclosure has been described with reference to a preferred embodiment. Obviously, modifications and alternations will occur to those of ordinary skill in the art upon reading and understanding the preceding detailed description. It is intended that the present disclosure be construed to include all such alternations and modifications insofar as they come within the scope of the appended claims or their equivalents.

What is claimed is:

1. A blood purification apparatus comprising:
   a blood purifier for performing blood purification;
   an arterial blood circuit has a proximal end connected to the blood purifier and a blood pump disposed in the arterial blood circuit;
   a venous blood circuit has a proximal end connected to the blood purifier;
   a dialysate introduction line introduces a dialysate into the blood purifier;
   a dialysate discharge line discharges the dialysate from the blood purifier;
   a dialysate infusing line has one end connected to a collection port formed in a predetermined part of the dialysate introduction line, and another end is connected to the arterial blood circuit or the venous blood circuit;
   a dialysate infusing pump disposed in the dialysate infusing line, the dialysate infusing pump supplies the dialysate of the dialysate introduction line to the arterial blood circuit or the venous blood circuit;
   a mechanism for forming a closed circuit in a flow route of the dialysate introduction line side, the closed circuit including the predetermined part formed with the collection port; and
   a determination device confirming the connection of the dialysate infusing line to the collection port by measuring a fluid pressure in the closed circuit while driving the dialysate infusing pump in a direction that applies a pressure to the closed circuit.

2. The blood purification apparatus according to claim 1, wherein a clamp device, capable of opening and closing the flow route, is disposed in the dialysate infusing line, and the connection confirmation of the dialysate infusing line and the opening and closing confirmation of the clamp device can be performed in the test process.

3. The blood purification apparatus according to claim 1, wherein a positive pressure is applied to the closed circuit by driving the dialysate infusing pump in a reverse rotation direction in the test process.

4. The blood purification apparatus according to claim 1, wherein the device for conducting a test process further comprising a measurement device capable of measuring a fluid pressure in the closed circuit state where the dialysate infusing pump is driven in the test process and a determination device for determining whether or not the dialysate infusing line is connected normally to the collection port based on a measured value of the measurement device.

5. The blood purification apparatus according to claim 1, wherein the pressure can be positive or negative.

* * * * *